US011708257B2

(12) United States Patent
Hayakawa

(10) Patent No.: US 11,708,257 B2
(45) Date of Patent: Jul. 25, 2023

(54) METHOD OF CLEANING AND STERILIZING DRINK FILLING APPARATUS

(71) Applicant: Dai Nippon Printing Co., Ltd., Tokyo (JP)

(72) Inventor: Atsushi Hayakawa, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 0 days.

(21) Appl. No.: 16/958,871

(22) PCT Filed: Jan. 11, 2019

(86) PCT No.: PCT/JP2019/000721
§ 371 (c)(1),
(2) Date: Jun. 29, 2020

(87) PCT Pub. No.: WO2019/142742
PCT Pub. Date: Jul. 25, 2019

(65) Prior Publication Data
US 2020/0339401 A1  Oct. 29, 2020

(30) Foreign Application Priority Data

Jan. 16, 2018 (JP) .................................. 2018-004863

(51) Int. Cl.
*B67C 3/00* (2006.01)
*B08B 7/04* (2006.01)
*B08B 9/032* (2006.01)

(52) U.S. Cl.
CPC ................ *B67C 3/001* (2013.01); *B08B 7/04* (2013.01); *B08B 9/032* (2013.01); *B08B 2209/032* (2013.01)

(58) Field of Classification Search
CPC ...... B67C 3/001; B08B 7/04; B08B 2209/032
See application file for complete search history.

(56) References Cited

U.S. PATENT DOCUMENTS

2014/0286822 A1* 9/2014 Hayakawa ................ A23L 3/18
422/1
2015/0298178 A1* 10/2015 Hayakawa .............. B08B 9/027
134/22.1

(Continued)

FOREIGN PATENT DOCUMENTS

JP 2007-022600 A1  2/2007
JP 2017-095114 A1  6/2017

(Continued)

OTHER PUBLICATIONS

International Search Report and Written Opinion (Application No. PCT/JP2019/000721) dated April 2, 2019.

*Primary Examiner* — Sharidan Carrillo
(74) *Attorney, Agent, or Firm* — Burr Patent Law, PLLC

(57) ABSTRACT

A method of cleaning and sterilizing a drink filling apparatus that includes drink supply piping that feeds a drink sterilized in a heating sterilization part into a filling machine includes performing a cleaning in place (CIP), in which a cleaner is circulated in the drink supply piping to remove a drink residue or the like on an interior of the drink supply piping, raising a temperature of the cleaner to a temperature required for a sterilizing in place (SIP), which is performed in succession to the CIP to sterilize the interior of the drink supply piping, from an early stage or middle stage of the CIP, then performing the SIP for the interior of the drink supply piping, and washing the cleaner away with aseptic water heated and sterilized in the heating sterilization part.

4 Claims, 8 Drawing Sheets

(56) References Cited

U.S. PATENT DOCUMENTS

| | | | |
|---|---|---|---|
| 2016/0121376 A1* | 5/2016 | Hayakawa | ............ B08B 9/0325 |
| | | | 422/3 |
| 2016/0185584 A1 | 6/2016 | Hayakawa et al. | |
| 2018/0208446 A1 | 7/2018 | Hayakawa et al. | |
| 2018/0334372 A1* | 11/2018 | Hayakawa | ................ B67C 7/00 |
| 2020/0277178 A1* | 9/2020 | Hayakawa | ................ B67C 3/00 |

FOREIGN PATENT DOCUMENTS

| | | | |
|---|---|---|---|
| WO | 2014/098058 A1 | 6/2014 | |
| WO | WO-2017047691 A1 * | 3/2017 | ............... A61L 2/04 |
| WO | 2017/111047 A1 | 6/2017 | |

* cited by examiner

METHOD OF CLEANING AND STERILIZING DRINK FILLING APPARATUS

BACKGROUND OF THE INVENTION

1. Field of the Invention

The present invention relates to a method of cleaning and sterilizing a drink filling apparatus that fills a container such as a PET bottle with tea, mineral water, fruit juice, a medicine, a food, a liquid food, a drink mixed with a solid or the like as a product.

2. Description of Related Art

When a drink filling apparatus fills a container such as a bottle with a product such as a drink, not only does a product sterilization process in which the product itself is sterilized to be aseptic have to be performed, but also the interior of drink supply piping including a surge tank, a liquid feeding pipe, and filling nozzles in the drink filling apparatus has to be cleaned and sterilized to be aseptic in advance.

With the drink supply piping of the drink filling apparatus, a CIP (Cleaning in Place) process for cleaning the interior of the drink supply piping and an SIP (Sterilizing in Place) process for sterilizing the interior of the drink supply piping are performed regularly or each time the kind of drink to be manufactured is changed (see Patent Document 1, for example).

The CIP is performed by passing a cleaner containing water and an alkali agent such as caustic soda as an additive through a flow path from the pipe line of the drink supply piping to the filing nozzles of the filling machine and then passing a cleaner containing water and an acid agent as an additive through the same flow path. The CIP is performed by circulating the cleaner in the drink supply piping while a heating sterilization part is keeping the cleaner at 80° C., for example. The CIP removes a residue of the previous product in the product supply piping, for example (see Patent Document 1, for example).

The SIP is a process to sterilize the interior of the drink supply piping before the product filling operation is started, and is performed by passing a heated steam or hot water through the drink supply piping cleaned by the CIP described above, for example. The heated steam or hot water is kept at 130° C., for example. The SIP sterilizes the interior of the drink supply piping and makes it aseptic (see Patent Document 1, for example).

When the product is passed through the drink supply piping after the CIP and the SIP are performed, a product sterilization process is performed by heating and sterilizing the product in a heating sterilization part (UHT: Ultra High-temperature) arranged along the drink supply piping. Then, a container such as a bottle can be filled with the sterilized product.

Conventionally, the CIP is performed by passing the cleaner from the pipe line of the drink supply piping to the filling nozzles of the filling machine, and the SIP is performed by passing the heated steam or hot water through the drink supply piping. However, a method of performing the CIP and the SIP in succession has been proposed (see Patent Document 2). According to the method, after the cleaning is completed, the cleaner used for the CIP is heated to a temperature for the SIP process, and the SIP is performed by circulating the heated cleaner.

CITATION LIST

Patent Literature

Patent Literature 1: Japanese Patent Laid-Open No. 2007-22600
Patent Literature 2: Japanese Patent Laid-Open No. 2017-95114

SUMMARY OF THE INVENTION

Technical Problem

By performing cleaning and sterilization of the drink filling apparatus and sterilization of the product in the manner described above, the quality of the aseptically packaged product can be properly and quickly assured.

However, according to a cleaning and sterilization method that performs the CIP, the SIP and the product sterilization process on the drink supply piping of the drink filling apparatus in succession, when transitioning from the CIP to the SIP, a rinsing process is performed to rinse the cleaner used in the CIP with water at room temperature. Therefore, the temperature of the heating sterilization part that performs the product sterilization process decreases and thus needs to be raised to a temperature required for the SIP before the SIP is started. Thus, there is a problem that it takes a long time to transition to the SIP. Furthermore, there is another problem that a switching operation including change of the UHT holding tube, replacement and inspection of filters at different positions, and disassembly and cleaning of the homogenizer is performed between the manufacturing step and the CIP, and the switching operation takes a very long time.

As described above, according to the conventional cleaning and sterilization method, products cannot be manufactured during the CIP or the SIP, so that the operability of the drink filling apparatus decreases, and the products cannot be efficiently manufactured. However, according to the method proposed in Patent Document 2, in which the cleaner used for the CIP is heated to the temperature for the SIP after the cleaning is completed, and the SIP is performed by circulating the heated cleaner, allows the CIP and the SIP to be performed in succession without wasting time in the transition from the CIP to the SIP. When the SIP with the heated cleaner ends, a rinse process is performed to rinse the cleaner remaining in the drink supply piping with aseptic water. Since the rinsing is performed with aseptic water, a unit for producing the aseptic water is needed. And in order to provide an aseptic water production unit, an additional investment is needed. Thus, there is a demand for a method of cleaning and sterilizing a drink filling apparatus that can perform the CIP and the SIP in succession and perform rinsing with aseptic water without the need for additional investment.

The present invention has been devised to solve these problems, and an object of the present invention is to provide a method of cleaning and sterilizing a drink filling apparatus that can efficiently manufacture products with an increased operability without the need for additional investment.

Solution to Problem

A method of cleaning and sterilizing a drink filling apparatus according to the present invention is a method of cleaning and sterilizing a drink filling apparatus that includes drink supply piping that feeds a drink sterilized in a heating sterilization part into a filling machine, the method comprising performing a cleaning in place (CIP), in which a cleaner is circulated in the drink supply piping to remove a drink residue or the like on an interior of the drink supply piping, raising a temperature of the cleaner to a temperature required for a sterilizing in place (SIP), which is performed in succession to the CIP to sterilize the interior of the drink supply piping, from an early stage or middle stage of the CIP, then performing the SIP for the interior of the drink supply piping, and washing the cleaner away with aseptic water, wherein the aseptic water is heated and sterilized in the heating sterilization part.

In the method of cleaning and sterilizing a drink filling apparatus according to the present invention, preferably, the CIP and the SIP are performed by circulating a cleaner in each of an upstream-side process path of the drink supply piping including a balance tank, the heating sterilization part and a manifold valve and a downstream-side process path of the drink supply piping including the manifold valve, an aseptic surge tank, head tank and the filling machine, and rinsing of the interior of the drink supply piping with the aseptic water is performed by flowing to the heating sterilization part, the manifold valve, the aseptic surge tank, the head tank, the filling machine and the manifold valve and discharging from the drink filling apparatus.

In the method of cleaning and sterilizing a drink filling apparatus according to the present invention, preferably, a condition of sterilization of the aseptic water in the heating sterilization part is comparable to or stricter than a condition of sterilization of the drink to be filled next.

DETAILED DESCRIPTION OF THE INVENTION

According to the present invention, in the drink filling apparatus, after a drink filling operation ends and before the next drink filling operation is started, the CIP for the interior of the drink supply piping of the drink filling apparatus is performed with a cleaner, the cleaner is then heated to a sterilization temperature required for the SIP, the SIP is performed with the heated cleaner, and after the SIP, the rinse process is performed to wash away any cleaner remaining in the drink supply piping with aseptic water sterilized in the heating sterilization part that sterilizes the drink. Therefore, no additional aseptic water production unit is needed, and the drink filling apparatus can be cleaned and sterilized with a reduced time for the transition from the CIP to the SIP. In addition, by setting the condition of production of the aseptic water in the heating sterilization unit to be comparable to the condition of sterilization of the drink to be filled next, the heating sterilization condition can be established during the rinsing of the interior of the drink supply piping, so that the next drink filling operation can be started in a shorter time.

DESCRIPTION OF EMBODIMENT

In the following, an embodiment of the present invention will be described with reference to the drawings.

A configuration of a drink filling apparatus will be first described, and a method of cleaning and sterilizing the apparatus and a product filling method for the apparatus will then be described.

Figure 1:
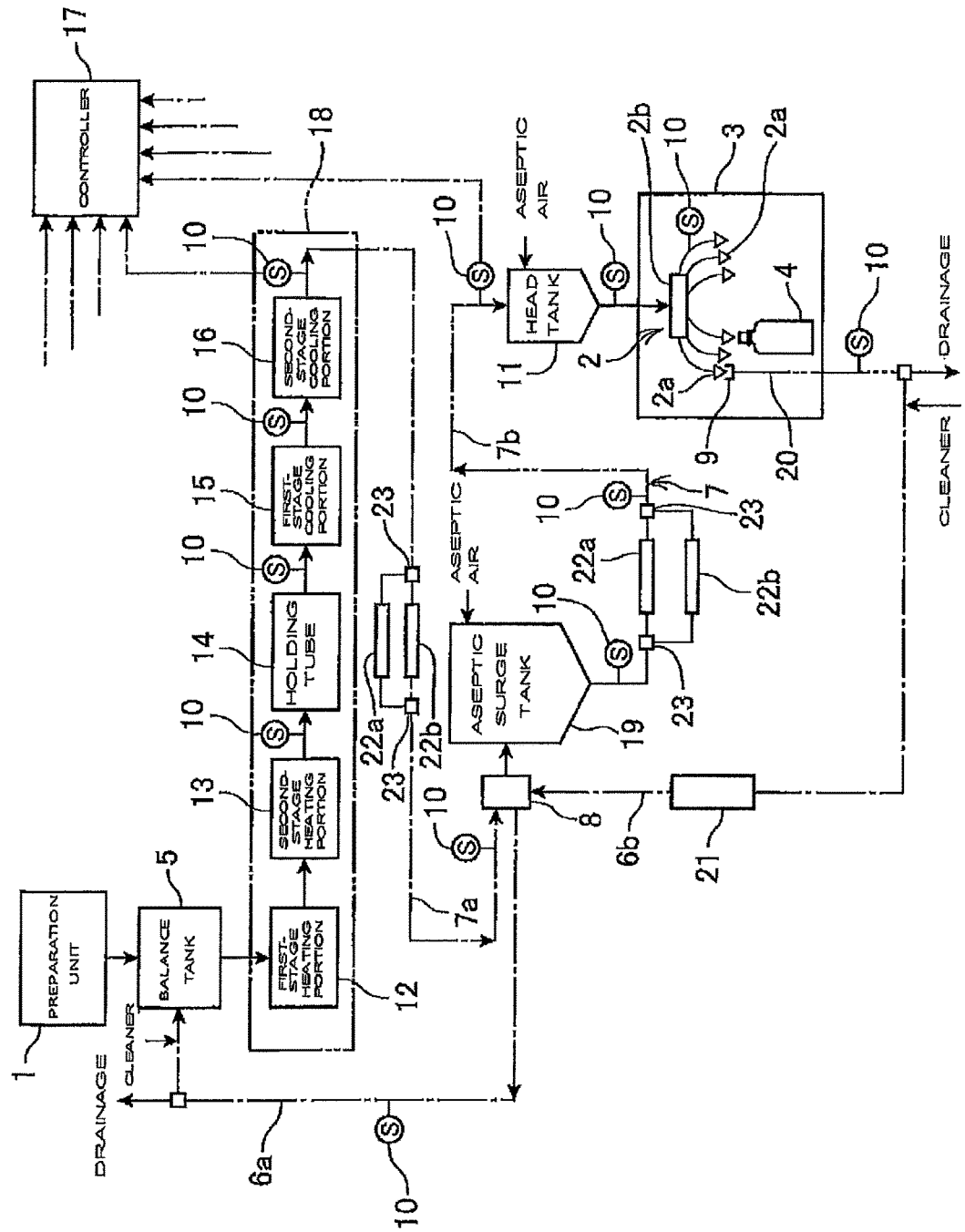
FIG. 1 is a block diagram showing a drink filling apparatus to which a cleaning and sterilization method according to the present invention is applied.

As shown in FIG. 1, the drink filling apparatus includes a preparation unit 1 for a drink as a product and a filling machine 2 that fills a bottle 4 with the drink. The preparation unit 1 and filling nozzles 2a in the filling machine 2 are coupled to each other by drink supply piping 7. The filling machine 2 is surrounded by an aseptic chamber 3.

The preparation unit 1 prepares a drink such as tea or fruit juice by mixing ingredients in desired proportions. The preparation unit 1 is a well-known device and therefore will not be described in detail herein.

The filling machine 2 includes a large number of filling nozzles 2a arranged around a wheel (not shown), which rotates at high speed in a horizontal plane. As the wheel rotates, the filling nozzles 2a rotate, and the drink is metered from the filling nozzles 2a into bottles 4 traveling below the filling nozzles 2a at a velocity adjusted to the circumferential velocity of the wheel. The filling machine 2 is also a well-known machine and therefore will not be described in detail herein.

In the drink filling apparatus, along the path of the drink supply piping 7 from the preparation unit 1 to the filling machine 2, a balance tank 5, a heating sterilization part (hereinafter, referred to also as UHT: Ultra High-temperature) 18, a manifold valve 8, an aseptic surge tank 19, and a head tank 11 are disposed in this order from upstream to downstream of the flow of the drink.

The heating sterilization part 18 includes a first-stage heating portion 12, a second-stage heating portion 13, a holding tube 14, a first-stage cooling portion 15 and a second-stage cooling portion 16, for example. The drink or water supplied from the balance tank 5 is gradually heated while fed from the first-stage heating portion 12 to the second-stage heating portion 13 until a target sterilization temperature is reached at an exit of the second-stage heating portion 13, kept at the sterilization temperature for a certain time in the holding tube 14, and then gradually cooled while fed from the first-stage cooling portion 15 to the second-stage cooling portion 16. The number of stages of heating portions or cooling portions can be increased or decreased as required. The heating sterilization part 18 may include a homogenizer capable of automatic washing. The homogenizer is preferably disposed between the first-stage heating portion, in which the temperature of the content of the product is about 50 to 70° C., and the second-stage heating portion, in which the temperature of the content of the product is about 60 to 150° C., or between the first-stage cooling portion and the second-stage cooling portion. In the former case, a common homogenizer can be used. In the latter case, however, an aseptic homogenizer is needed. The heating sterilization part 18 can be of any type, such as a shell-and-tube heat exchanger or a plate heat exchanger. Furthermore, not only the indirect heating method described above but also the direct heating method can be used.

The balance tank 5, the manifold valve 8, the aseptic surge tank 19 and the head tank 11 are well-known devices and therefore will not be described in detail herein. The aseptic surge tank 19 and the head tank 11 are provided with equipment to which aseptic air is supplied.

Next, a process path along which CIP and SIP are performed will be described. As shown by a bold line in FIG. 2, an upstream-side piping section 7a of the drink supply piping 7, which extends from the balance tank 5 to the manifold valve 8 through the heating sterilization part 18, is provided with an upstream-side feedback path 6a to form an upstream-side process path, which is a circulation path for the CIP or SIP.

Figure 3:
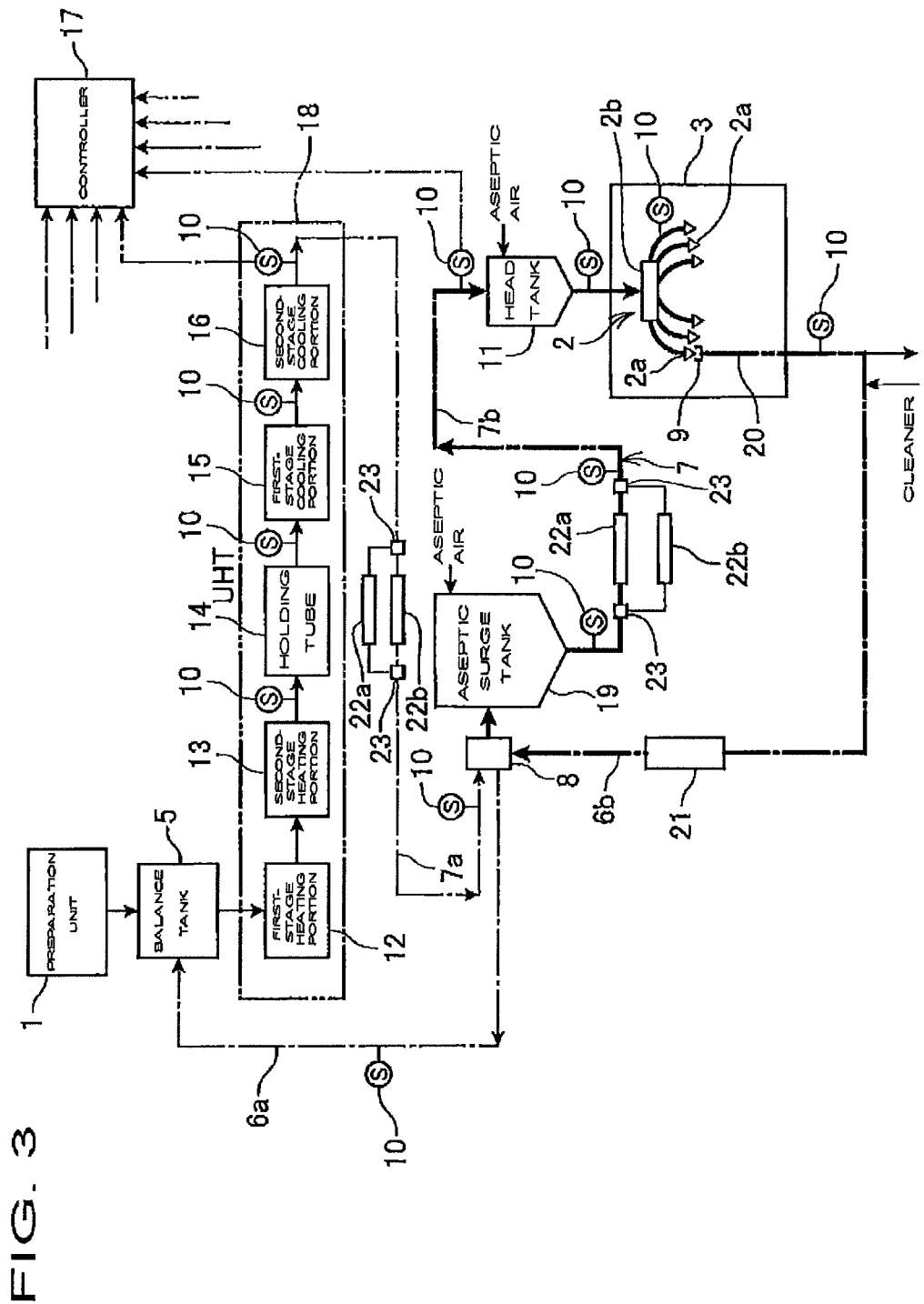
FIG. 3 is a block diagram for illustrating a CIP or SIP performed for a downstream-side process path of the drink supply piping in the cleaning and sterilization method according to the present invention.

As shown by a bold line in FIG. 3, a downstream-side piping section 7b, which extends from the manifold valve 8 to the aseptic surge tank 19, then to the head tank 11, then to the filling machine 2 and then back to the manifold valve 8, is provided with a downstream-side feedback path 6b to form a downstream-side process path, which is a circulation path for the CIP or SIP.

The upstream-side piping section 7a is provided with temperature sensors 10 at positions including a position where the temperature is less likely to increase during the SIP. For example, the temperature sensors 10 can be disposed at positions along the pipe line from the second-stage heating portion 13 in the heating sterilization part 18 to the manifold valve 8, such as positions in the heating sterilization part 18, a position at the outlet of the second-stage cooling portion 16, and a position at the inlet of the manifold valve 8. The temperature sensors 10 are disposed at these positions. Temperature information from the temperature sensors 10 is transmitted to a controller 17.

The balance tank 5 can be any tank, such as an open tank for which the filling temperature is prescribed to be lower than 100° C. or a tank that is a first class pressure vessel (Occupational Safety and Health Regulation Section (v)) to which a fluid at a temperature of 100° C. or higher can be fed. When the open tank is used, a cooling unit is preferably provided on the upstream-side feedback path 6a between the manifold valve 8 and the balance tank 5.

As shown by the bold line in FIG. 3, the downstream-side piping section 7b is also provided with temperature sensors 10 at positions including a position where the temperature is less likely to increase during the SIP. For example, the temperature sensors 10 can be disposed at positions along the pipe line from the aseptic surge tank 19 to the filling nozzles 2a, such as a position in the vicinity of the outlet of the aseptic surge tank 19, a midway bent point, positions in the vicinities of the inlet and outlet of the head tank 11, positions between a manifold 2b and the filling nozzles 2a in the filling machine 2. The temperature sensors 10 are disposed at these positions. Temperature information from the temperature sensors 10 is transmitted to the controller 17.

In the downstream-side piping section 7b, a cup 9 is provided for an opening of each filling nozzle 2a in the filling machine 2 for the CIP or SIP, and the cup 9 can be brought closer to and separated from the filling nozzle 2a. To perform the CIP or SIP, an actuator (not shown) joins each cup 9 to the opening at the tip end of the filling nozzle 2a in the filling machine 2 to connect a leading end of a drain tube 20 to the opening of the filling nozzle 2a.

The drink supply piping 7 can include various switching valves, liquid feeding pumps or other components in addition to the manifold valve 8 and the actuator (not shown), and these components are also controlled by the controller 17.

The CIP or SIP may not be separately performed for the upstream-side piping section and the downstream-side piping section, and the process path may be formed by the drink supply piping 7 including the balance tank 5, the heating sterilization part 18, the manifold valve 8, the aseptic surge tank 19, the head tank 11 and the filling machine 2 and the circulation path from the filling machine 2 to the balance tank 5. That is, the process path may be the circulation path including the upstream-side piping section 7a, the downstream-side piping section 7b, the downstream-side feedback path 6b and the upstream-side feedback path 6a.

Next, a cleaning and sterilization method for the drink filling apparatus described above, a method of transition from the CIP to the SIP, a method of rinsing, and a drink product manufacturing step will be described with reference to FIGS. 2 to 7.

(CIP)

When an operation button on a panel (not shown) of the controller 17 is manipulated, the CIP is performed for each of the upstream-side piping section and the downstream-side piping section of the drink supply piping 7 in a predetermined procedure. The CIP is performed by flowing an alkali cleaner that contains a mixture of water and an alkali agent such as caustic soda (sodium hydroxide), potassium hydroxide, sodium carbonate, sodium silicate, sodium phosphate, sodium hydrochloride, a surface active agent or a chelating agent (sequestering agent) such as sodium gluconate or ethylenediaminetetraacetic acid (EDTA) and is supplied from a cleaner supply source (not shown) through the drink supply piping 7, the upstream-side feedback path 6a and the downstream-side feedback path 6b and then flowing an acid cleaner that contains a mixture of water and a nitrate-based or phosphate-based acid agent and is supplied from a cleaner supply source (not shown) through the drink supply piping 7, the upstream-side feedback path 6a and the downstream-side feedback path 6b.

The alkali cleaner may be lithium carbonate, ammonium carbonate, magnesium carbonate, calcium carbonate, propylene carbonate or a mixture thereof. However, the alkali cleaner is not limited to those substances. For example, the alkali cleaner may be a bicarbonate such as sodium bicarbonate, potassium bicarbonate, lithium bicarbonate, ammonium bicarbonate, magnesium bicarbonate or calcium bicarbonate, a sesquicarbonate such as sodium sesquicarbonate, potassium sesquicarbonate or lithium sesquicarbonate, or a mixture thereof.

The acid cleaner may not be the nitric acid or phosphoric acid described above but may also be hydrochloric acid, sulfuric acid, acetic acid, citric acid, lactic acid, formic acid, glycolic acid, methanesulfonic acid, sulfamic acid or a mixture thereof. However, the acid cleaner is not limited to those substances.

The cleaners may contain various bleaching agents such as hypochlorite, hydrogen peroxide, peracetic acid, peroctanoic acid, persulfate, perborate, hydrosulfite or thiourea dioxide, or percarbonate, for example. The cleaners may further contain a water softener such as aluminosilicate or polycarboxylate, or an antiredeposition agent such as sodium phosphate, sodium polyacrylate or sodium carboxylate. Furthermore, the cleaners may contain an enzyme, a solvent, a fatty acid, a foam control agent, an active oxygen source or the like.

The cleaners can be used in other sequences than the sequence described above in the CIP. For example, the alkali cleaner may be used after the acid cleaner is used, or the CIP may be performed by flowing only the acidic cleaner or the alkali cleaner.

Figure 2:
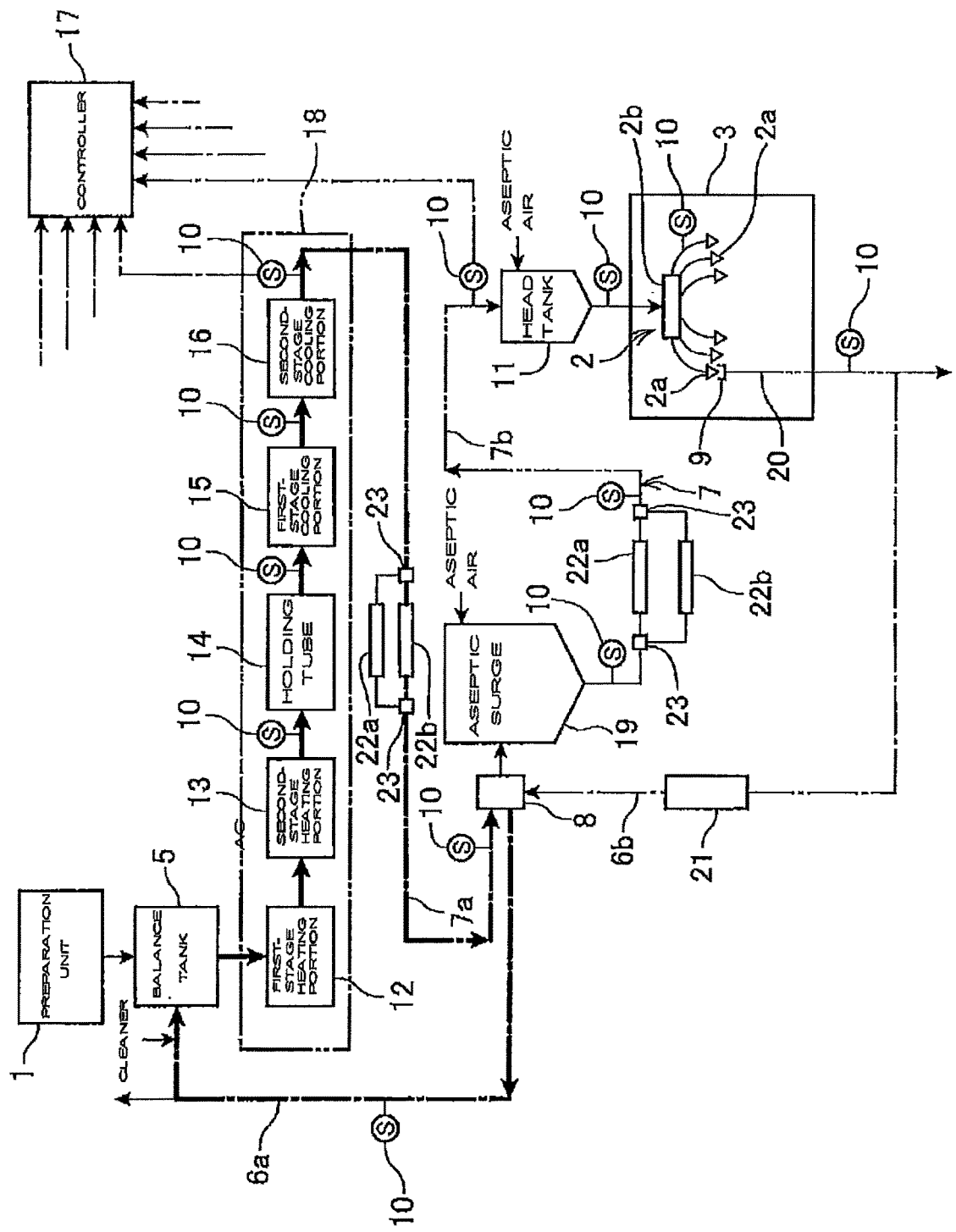
FIG. 2 is a block diagram for illustrating a CIP or SIP performed for an upstream-side process path of drink supply piping in the cleaning and sterilization method according to the present invention.

The CIP for the upstream-side process path is performed by circulating the cleaners supplied from the cleaner supply sources (not shown) through the upstream-side process path including the balance tank 5, the heating sterilization part 18 and the manifold valve 8 provided in the upstream-side piping section 7a of the drink supply piping 7 as shown in FIG. 2. To activate the cleaners, the heating sterilization part 18 provided on the upstream-side piping section 7a heats the cleaners to a predetermined temperature (80° C., for example). The cleaners are constantly or intermittently supplied in a constant amount from the respective cleaner supply sources (not shown) and remove drink residues from the previous operation on the interior of the drink supply piping 7 while circulating in the drink supply piping 7. The cleaners may be discharged from the apparatus as appropriate. After the cleaners at a predetermined temperature are passed for a predetermined time, the CIP ends. The completion of the CIP is managed by the controller 17, and then transition to the SIP occurs.

The CIP for the downstream-side process path is performed by circulating the cleaners supplied from the cleaner supply sources (not shown) through the downstream-side process path including the manifold valve 8, the aseptic surge tank 19, the head tank 11 and the filling machine 2 provided along the drink supply piping 7 as shown in FIG. 3. To activate the cleaners, a heating unit 21 provided on the downstream-side piping section 7b heats the cleaners to a predetermined temperature (80° C., for example). The cleaners are constantly or intermittently supplied in a constant amount from the respective cleaner supply sources (not shown) and remove drink residues from the previous operation on the interior of the drink supply piping 7 while circulating in the drink supply piping 7. The cleaners may be discharged from the apparatus as appropriate. After the cleaners at a predetermined temperature are passed for a predetermined time, the CIP ends. The completion of the CIP is managed by the controller 17, and then transition to the SIP occurs.

Before the CIP for the downstream-side process path is performed, the cups 9 are joined to the openings of the filling nozzles 2a and the drain tubes 20 are connected to the filling nozzles 2a, thereby allowing the cleaners to circulate through the downstream-side feedback path 6b, which is the downstream-side process path.

(SIP)

When the CIP ends, the SIP is performed for each of the upstream-side process path and the downstream-side process path in a predetermined procedure. Before the SIP, as with the CIP, the manifold valve 8 disconnects the upstream-side piping section 7a and the downstream-side piping section 7b from each other as required.

The SIP for the upstream-side process path and the SIP for the downstream-side process path can be performed in sequence or in parallel with each other.

First, the SIP performed for the upstream-side process path will be described. The liquid feeding pump used for the CIP is not stopped, and while the cleaner used in the CIP is circulating in the upstream-side process path, the cleaner is heated to a required temperature for the SIP by the heating sterilization part 18, and the SIP is achieved by the cleaner heated to the higher temperature circulating in the upstream-side process path. In this step, since the liquid feeding pump is not stopped, the temperature of the heating sterilization part 18 raised and set in the CIP does not decrease but is further raised to a temperature for the SIP. Thus, the temperature in the upstream-side piping section 7a including the heating sterilization part 18 does not decrease during the transition from the CIP to the SIP.

When the cleaner is flowing in the upstream-side process path, the temperature sensors 10 disposed at different positions along the upstream-side piping section 7a transmit temperature information to the controller 17 at regular time intervals. In this embodiment, when the drink, which is a product liquid with which the bottle 4 is to be filled, has a pH of 4.6 or higher, a reference temperature Tr can be set at 121.1° C. and the Z value can be set at 10° C. as temperature conditions for sterilization.

The last cleaner used in the CIP is heated to the required temperature for the SIP in the heating sterilization part 18, and when the temperature at each of the different positions along the upstream-side piping section 7a reaches 121.1° C., the controller 17 starts calculating the F value at the position according to the following formula.

$$F = \int_{t_0}^{t_1} 10^{(T-Tr)/Z} dt \quad \text{[Formula 1]}$$

(wherein T is an optional sterilizing temperature (° C.), $10^{(T-Tr)/Z}$ is a fatality rate at the optional temperature T, Tr is a reference temperature (° C.), and Z is a Z value (° C.).)

When the minimum F value of the F values calculated according to the formula described above reaches a target value, it is determined that sterilization of the upstream-side piping section 7a is completed. The sterilization method is not limited to the sterilization method based on the calculated F value described above but may be a known sterilization method based on temperature and time, for example.

In the formula for calculating the F value described above, the reference temperature Tr and the Z value can be changed according to the kind of the drink, which is a product liquid. For example, when the pH of the product liquid is equal to or higher than 4 and lower than 4.6, the reference temperature Tr can be 85° C., and the Z value can be 7.8° C. When the pH of the product liquid is lower than 4, the reference temperature Tr can be 65° C., and the Z value can be 5° C. The values to be substituted into the formula described above can be changed as appropriate according to the ease of development of microorganisms, the temperature during distribution or the like of the product liquid, such as tea, mineral water or a chilled drink. Thus, the required temperature for SIP varies with the kind of the drink to be handled next. Therefore, with regard to the transition from the CIP process to the SIP process, if the temperature required for SIP may be low, the CIP may be performed at a higher temperature than the SIP.

The SIP for the upstream-side piping section 7a may not be performed in succession to the CIP. The product also may not be manufactured immediately after the SIP. The drink filling apparatus may enter into a standby state for the subsequent manufacturing operation after the upstream-side piping section 7a is sterilized by aseptic water sterilized to have a sterilization value equal to or higher than that required for the drink to be manufactured next to prepare to feed the aseptic water to the downstream-side piping section 7b.

When or before the SIP for the upstream-side piping section 7a is started, the SIP for the downstream-side process path including the aseptic surge tank 19 is started.

Figure 6:
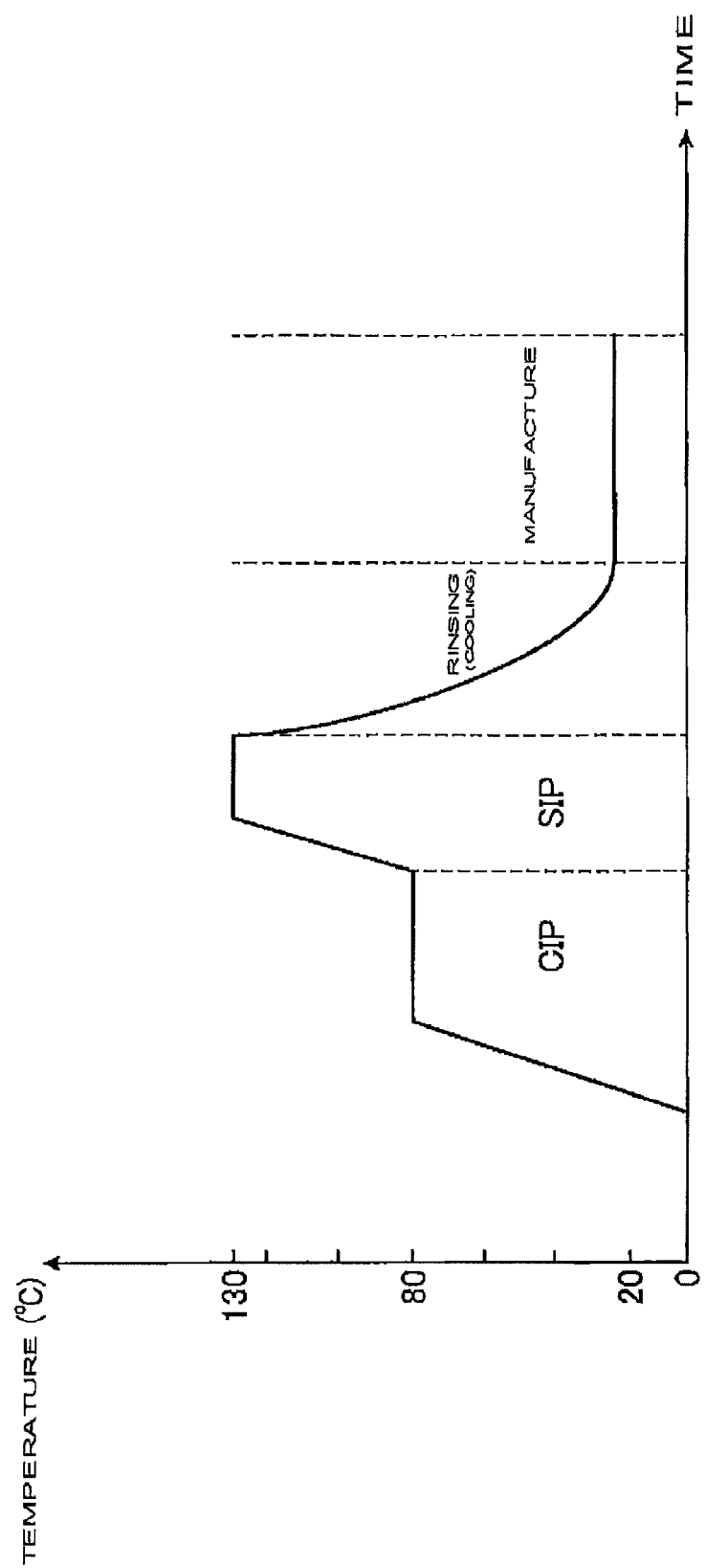
FIG. 6 is a graph for illustrating a variation in temperature of the filling machine in the CIP, the SIP and the rinsing and a drink filling step in the cleaning and sterilization method according to the present invention.

Next, the SIP performed for the downstream-side process path will be described. The liquid feeding pump used for the CIP is not stopped, and while the cleaner used in the CIP is circulating in the downstream-side process path, the cleaner is heated to a required temperature for the SIP by the heating unit 21, and the SIP is achieved by the cleaner circulating in the downstream-side process path. In this step, since the liquid feeding pump is not stopped, the temperature in the downstream-side piping section 7b raised in the CIP does not decrease, and the cleaner is heated to the required temperature for the SIP. Thus, unlike the conventional method shown in FIG. 7, the temperature in the downstream-side piping section 7b including the filling machine 2 does not decrease during the transition from the CIP to the SIP. That is, as shown in FIG. 6, the temperature in the downstream-side piping section 7b including the filling machine 2 does not decrease during the transition from the CIP to the SIP.

When the cleaner is flowing in the downstream-side process path, the temperature sensors 10 disposed at different positions along the downstream-side piping section 7b including the filling nozzles 2a transmit temperature information to the controller 17 at regular time intervals. In this embodiment, when the drink, which is a product liquid with which the bottle 4 is to be filled, has a pH of 4.6 or higher, the reference temperature Tr can be set at 121.1° C. and the Z value can be set at 10° C. as temperature conditions for sterilization.

The last cleaner used in the CIP is heated to the required temperature for the SIP by the heating unit 21, and when the temperature at each of the different positions along the downstream-side piping section 7b reaches 121.1° C., the controller 17 starts calculating the F value at the position according to the following formula.

$$F=\int_{t_0}^{t_1} 10^{(T-Tr)/Z} dt \quad \text{[Formula 2]}$$

(wherein T is an optional sterilizing temperature (° C.), $10^{(T-Tr)/Z}$ is a fatality rate at the optional temperature T, Tr is a reference temperature (° C.), and Z is a Z value (° C.).)

When the minimum F value of the F values calculated according to the formula described above reaches a target value, it is determined that sterilization of the downstream-side piping section 7b is completed. The sterilization method is not limited to the sterilization method based on the calculated F value described above but may be a known sterilization method based on temperature and time, for example.

In the formula for calculating the F value described above, the reference temperature Tr and the Z value can be changed according to the kind of the drink, which is a product liquid. For example, when the pH of the product liquid is equal to or higher than 4 and lower than 4.6, the reference temperature Tr can be 85° C., and the Z value can be 7.8° C. When the pH of the product liquid is lower than 4, the reference temperature Tr can be 65° C., and the Z value can be 5° C. The values to be substituted into the formula described above can be changed as appropriate according to the ease of development of microorganisms, the temperature during distribution or the like of the product liquid, such as tea, mineral water or a chilled drink. Thus, the required temperature for SIP varies with the kind of the drink to be handled next. Therefore, with regard to the transition from the CIP process to the SIP process, if the temperature required for SIP may be low, the CIP may be performed at a higher temperature than the SIP.

Under a condition that the temperature in the SIP is higher than 100° C., the downstream-side process path may be cooled with aseptic air after the SIP is completed. In this step, the downstream-side process path is cooled by supplying aseptic air (or nitrogen) filtered and sterilized through a sterilization filter until the temperature in the aseptic surge tank 19 and the head tank 11 is lower than 100° C. In this step, at the same time, a coolant such as water may be supplied to jackets of the aseptic surge tank 19 and the head tank 11 to cool the downstream-side process path.

(Rinsing)

After the SIP is completed, the cleaner used in the SIP is discharged from the upstream-side process path and the downstream-side process path at the same time or in sequence, and the cleaner remaining in the drink supply piping 7, the upstream-side feedback path 6a and the downstream-side feedback path 6b is washed away with aseptic water. The upstream-side process path may be left unrinsed until the SIP for the downstream-side process path is completed, and after the SIP for the downstream-side process path is completed, the upstream-side process path and the downstream-side process path may be coupled to each other and rinsed at the same time. Alternatively, the upstream-side process path may be first rinsed and left with aseptic water circulating therein, and after the SIP for the downstream-side process path is completed, the upstream-side process path and the downstream-side process path may be coupled to each other to feed the aseptic water in the upstream-side process path to the downstream-side process path, thereby rinsing the downstream-side process path.

Figure 4:
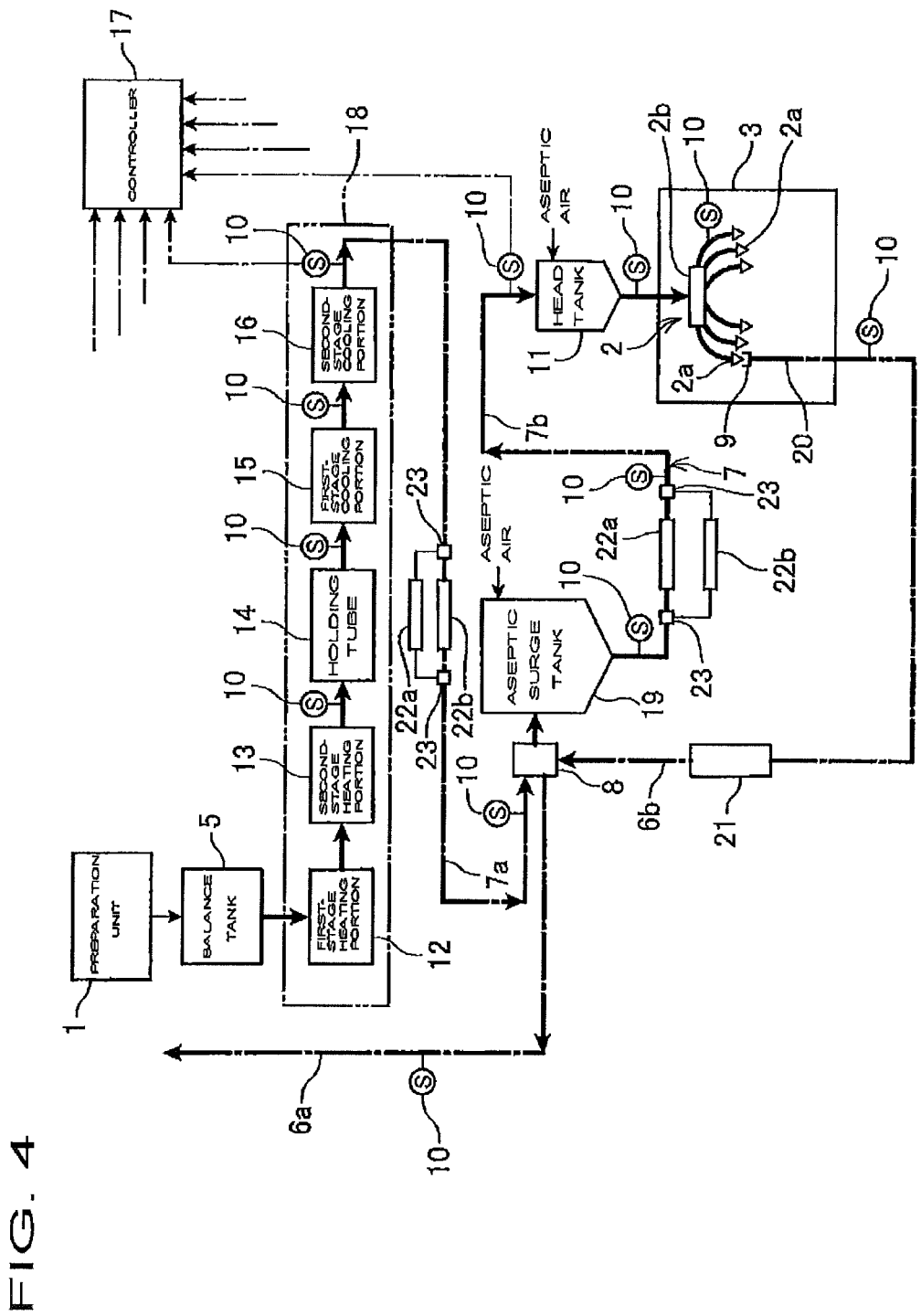
FIG. 4 is a block diagram for illustrating rinsing of the entire drink supply piping with aseptic water in the cleaning and sterilization method according to the present invention.

The CIP and SIP are performed by circulating the cleaners in each of the upstream-side process path of the drink supply piping 7 including the balance tank 5, the heating sterilization part 18 and the manifold valve 8 and the downstream-side process path of the drink supply piping 7 including the manifold valve 8, the aseptic surge tank 19, the head tank 11 and the filling machine 2. However, as shown in FIG. 4, rinsing of the interior of the drink supply piping 7 with aseptic water is performed by flowing the aseptic water to the upstream-side feedback path 6a through the heating sterilization part 18, the manifold valve 8, the aseptic surge tank 19, the head tank 11, the filling machine 2, the downstream-side feedback path 6b and the manifold valve 8 to wash the cleaner away, and discharging the rinsing liquid from the drink filling apparatus.

The aseptic water is produced by supplying water or pure water into the balance tank 5 and heating and sterilizing the water or pure water under a sterilization condition that is comparable to or stricter than the sterilization condition for the drink to be filled next in the heating sterilization part 18. Since the aseptic water is produced under the sterilization condition comparable to that for the drink to be filled next, the sterilization condition of the heating sterilization part 18 is stabilized and the downstream-side piping section 7b is cooled while the rinsing is performed, and the drink can be sterilized and the product can be manufactured immediately after the rinsing is completed.

FIG. 6 is a graph showing a variation in temperature of the filling machine 2 in the CIP, the SIP and the rinsing of the downstream-side piping section 7b and a drink filling step (manufacturing step). After the CIP, the cleaner is heated to the required temperature for the SIP. After the SIP is completed, the temperature decreases as the rinsing proceeds. When the rinsing is completed and the temperature of the filling machine 2 is settled at room temperature, the bottles 4 can be immediately aseptically filled with the drink that has been sterilized and settled at room temperature. Neither time nor energy is wasted between the CIP and the manufacturing step of filling the bottles 4 with the drink.

Figure 7:
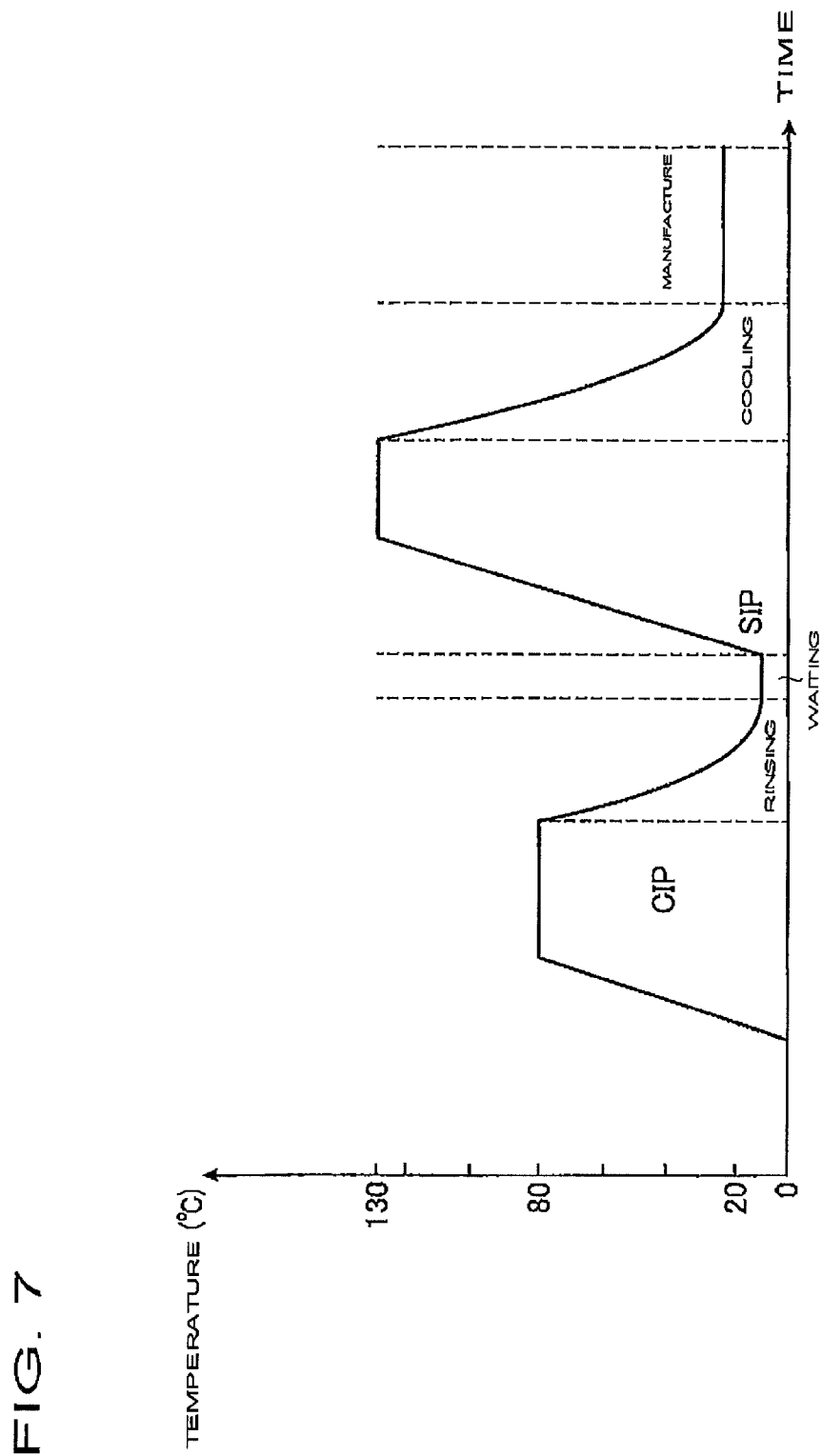
FIG. 7 is a graph for illustrating a variation in temperature of the filling machine in the CIP, the SIP and the rinsing and the drink filling step in a conventional cleaning and sterilization method.

FIG. 7 shows a variation in temperature of the filling machine 2 in the CIP, the SIP, the rinsing and the drink filling step (manufacturing step) in the conventional cleaning and sterilization method. The cleaner is heated to perform the CIP, and then rinsing with water or pure water that is not aseptic water is performed to wash the cleaner away. The water used for the rinsing is water and therefore is at room temperature, so that the filling machine 2, which has been at a higher temperature because of the CIP with the heated cleaner, is cooled by the rinsing water and substantially settled at room temperature when the rinsing is completed. After that, heated water or heated steam is circulated for the SIP and heats the filling machine 2 again. The filling machine 2 thus heated in the SIP needs to be cooled in order to aseptically fill the bottles 4 with the drink, and aseptic air or water is flowed to cool the filling machine 2. In this way, the conventional method requires longer times than the present invention to heat the drink supply piping 7 including the heating sterilization part 18 and the filling machine 2 that is cooled in the rinsing and to cool the section of the drink supply piping 7 that is downstream of the first-stage cooling portion 15 of the heating sterilization part 18 after the SIP. In addition, since heating and cooling are each performed twice, a larger amount of energy is required compared with the method shown in FIG. 6.

Figure 8:
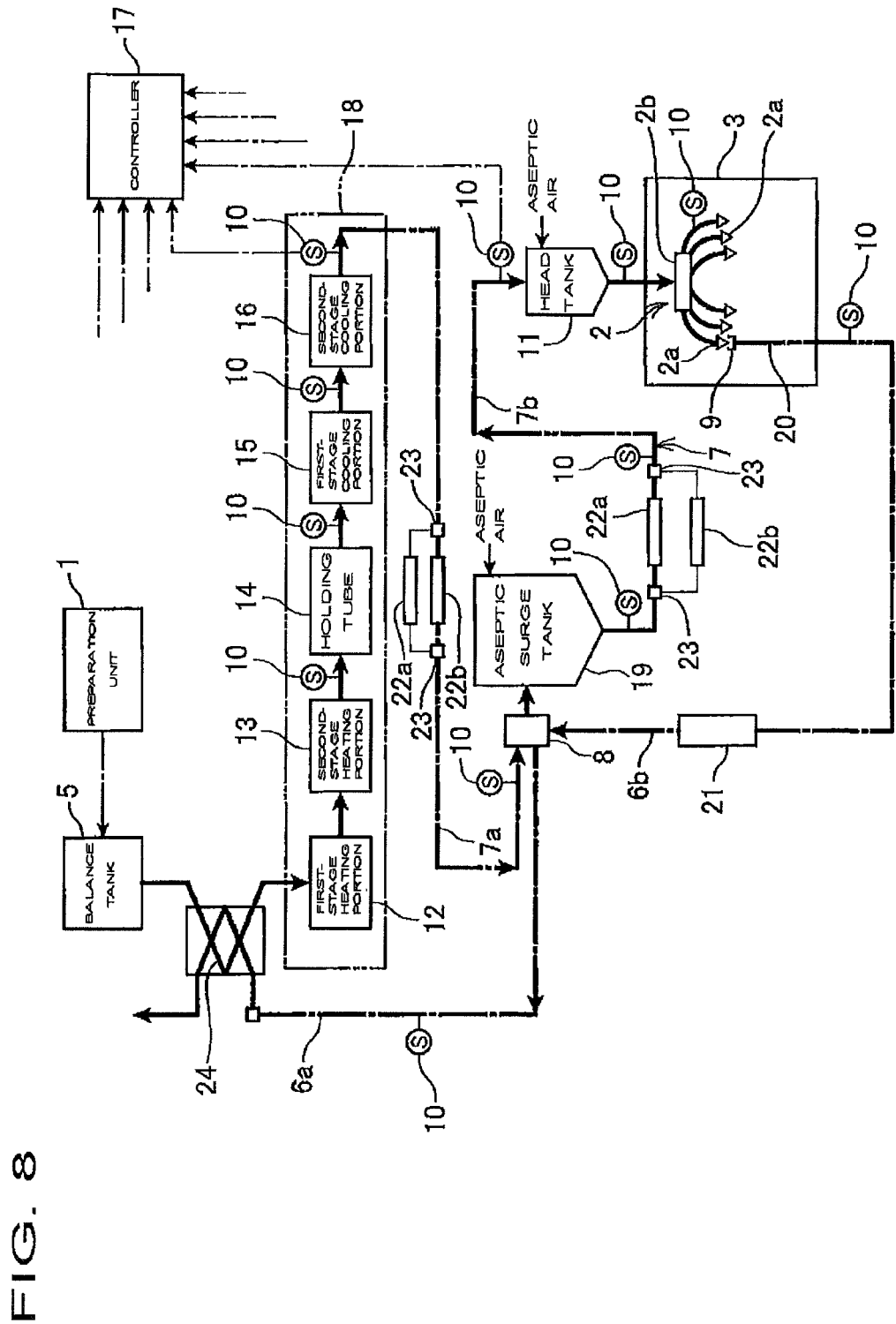
FIG. 8 is a block diagram for illustrating a modification of the rinsing of the entire drink supply piping with aseptic water in the cleaning and sterilization method according to the present invention.

Furthermore, as shown in FIG. 8, a heat exchanger 24 may be arranged between the heating sterilization part 18 and the balance tank 5 (or at a position preceding the balance tank 5) as required. The heat exchanger 24 can exchange heat between the cleaner for cleaning or sterilizing the interior of the drink supply piping 7 raised in temperature in the heating sterilization part 18 or the water for rinsing the interior of the drink supply piping 7 raised in temperature in the heating sterilization part 18 and the water or pure water at a lower temperature supplied from the balance tank 5, thereby raising the temperature of the water or pure water supplied from the balance tank 5 to the heating sterilization part 18. In this way, the heat exchanger 24 can reduce the burden on the heating sterilization part 18 when raising the temperature of the water or pure water and improve the thermal efficiency.

Immediately after the rinsing is started, the first-stage heating portion 12 and the second-stage heating portion 13, which have been heating the cleaner for the SIP for the upstream-side process path, can heat the water or pure water to a set temperature. However, the first-stage cooling portion 15 and the second-stage cooling portion 16, which have not been operating, and whose flow path is under the temperature condition for the SIP, takes some time to stabilize the cooling. However, the cooling is stabilized while the rinsing is performed. Once the cleaner is completely removed, the rinsing step can be ended, the drink to be filled next can be immediately sterilized and cooled, and the bottles 4 can be filled with the drink.

When the cleaner in the upstream-side process path and the downstream-side process path is removed with the aseptic water, and the cleaner in the filling nozzles 2a of the filling machine 2 is completely replaced by the aseptic water, the aseptic water is fed from the upstream-side piping section 7a to the upstream-side feedback path 6a through the manifold valve 8 and circulated in the upstream-side process path. Feeding of the aseptic water to the downstream-side piping section 7b is stopped. Furthermore, at the same time or after that, aseptic air is supplied into the drink supply piping 7 including the aseptic surge tank 19, the head tank 11, the upstream-side piping section 7a and the downstream-side piping section 7b while removing the aseptic water remaining in the aseptic surge tank 19, the head tank 11 and the downstream-side piping section 7b, thereby keeping the interior of the drink supply piping 7 including the aseptic surge tank 19, the head tank 11, the upstream-side piping section 7a and the downstream-side piping section 7b, in which the SIP has been performed, at a positive pressure and maintaining the aseptic condition in the drink supply piping 7. Furthermore, after the rinsing is completed, the actuator (not shown) removes the cups 9 from the openings of the filling nozzles 2a.

The downstream-side piping section 7b of the drink supply piping 7 is cooled by being rinsed with the aseptic water. However, in order to prevent the pressure in the aseptic surge tank 19 and the head tank 11 from decreasing due to rapid cooling, the downstream-side piping section 7b of the drink supply piping 7 is preferably cooled under pressure by supplying aseptic air into the tanks. After the temperature of the tanks is lowered to about 30° C. to 90° C., and the cooling is completed, the aseptic water remaining in the tanks and the piping is blown off by aseptic air while maintaining the positive pressure, and the drink is received. The tanks may be quickly cooled by supplying water or chiller water to jackets of the tanks in parallel with the cooling process by the rinsing. If it is difficult to discharge the aseptic water from the drink supply piping 7, the drink can also be fed into the drink supply piping 7, and any diluted drink alone can be discharged from the filling machine 2 before the manufacture is started.

If the drink to be filled next is a carbonated drink, the aseptic water is fed from a vicinity of the aseptic surge tank 19 to the head tank 11 and the filling nozzles 2a through a carbonated drink line (not shown). On the carbonated drink line, the aseptic water is further cooled (to 1 to 5° C.) by chiller water. Thus, the remaining heat from the SIP can be completely removed, and foaming of the carbon dioxide gas can be reduced during filling.

(Manufacturing Step)

After the rinsing ends, the drink flowing from the heating sterilization part 18 through the upstream-side piping section 7a is stored in the aseptic surge tank 19, and a manufacturing step of filling the bottles 4 with the drink flowing therefrom through the downstream-side piping section 7b is started.

Figure 5:
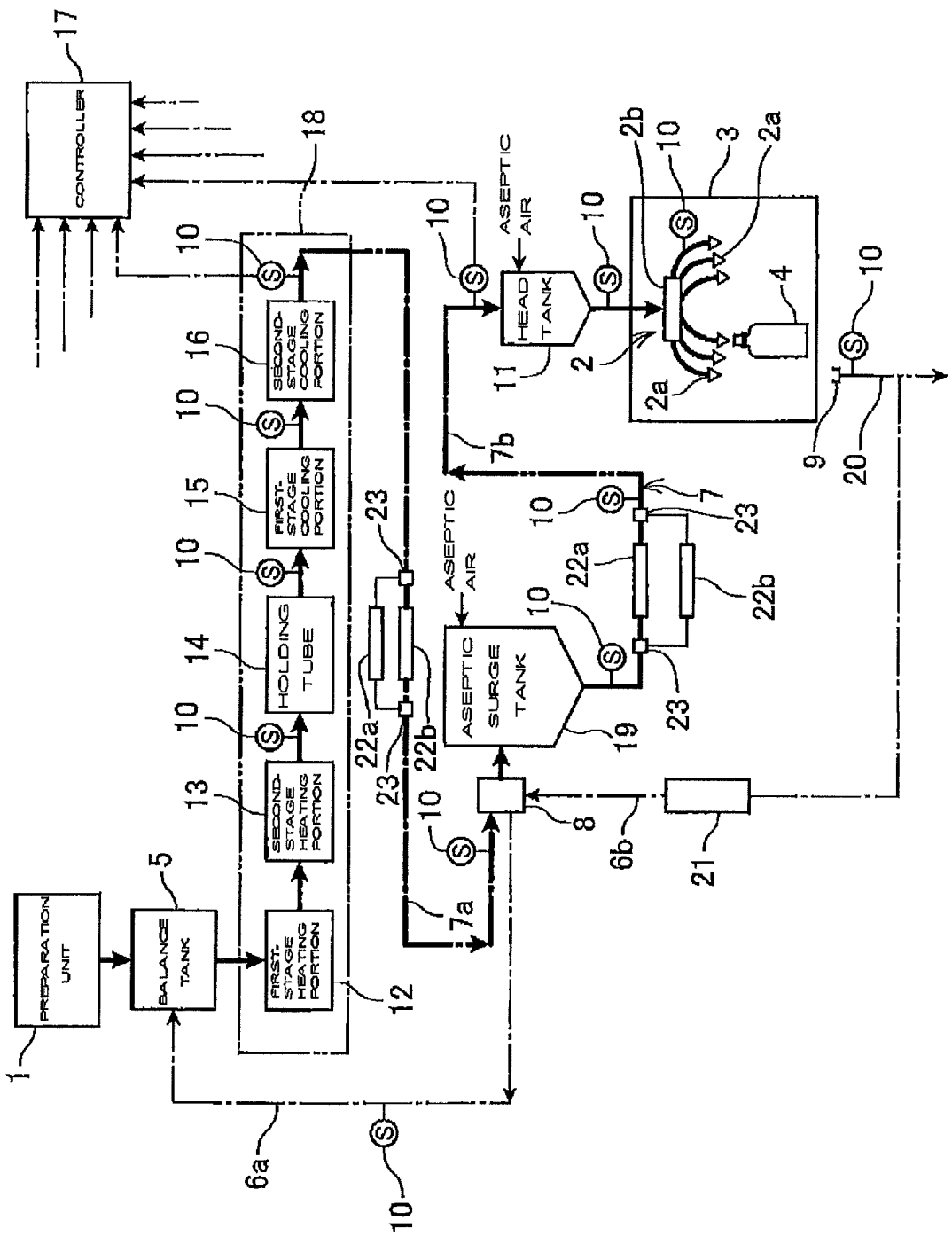
FIG. 5 is a block diagram for illustrating manufacture of a product by filling a bottle with a drink.

As shown by a bold line in FIG. 5, in the manufacturing step, the drink prepared in the preparation unit 1 flows to the interior of the filling machine 2 through the sterilized upstream-side piping section 7a and downstream-side piping section 7b of the drink supply piping 7, and the bottles 4 as containers are filled with the drink through the filling nozzles 2a in the filling machine 2. The bottles 4 filled with the drink are capped by a capper (not shown) and then fed out of the drink filling machine.

The drink supply piping 7 is preferably provided with a filtering device that filters out foreign matters in the product or product residues to be removed in the CIP. The filtering device includes a first filtering device 22a and a second filtering device 22b arranged in parallel with each other, and the first filtering device 22a and the second filtering device 22b include a filtering member formed by a metal filter, such as a stainless steel filter. The filtering device further includes switching devices 23 that automatically or manually switch between the first filtering device 22a and the second filtering device 22b.

The first filtering device 22a and the second filtering device 22b are preferably metal filters such as stainless steel filters and preferably differ in mesh fineness (mesh size). Preferably, for example, the first filtering device 22a includes a metal filter of 100 to 400 mesh capable of removing finer foreign matters, and the second filtering device 22b includes a rougher metal filter of 10 to 100 mesh capable of appropriately allowing flesh or pulp in the product to pass therethrough. By using filtering devices of different counts for the first filtering device 22a and the second filtering device 22b as described above, foreign matters can be appropriately removed from each individual product to be manufactured.

In addition, the switching devices 23 allow switching between the first filtering device 22a and the second filtering device 22b. Since the switching devices 23 are provided, while the first filtering device 22a is being used for filling with the product as shown in FIG. 5, a cleaning step for the second filtering device 22b can be performed to remove foreign matters from the second filtering device 22b. Thus, during manufacture of the product, the filtering device can be efficiently cleaned and inspected. After the cleaning and inspection of the filters, the CIP or the SIP can be separately performed. The switching devices 23 can be set to feed liquid to both the first filtering device 22a and the second filtering device 22b. In that case, the CIP or the SIP for both the first filtering device 22a and the second filtering device 22b can be performed at the same time.

As shown in FIG. 1, for example, the filtering device may be disposed between the second-stage cooling portion (final cooling portion) 16 and the manifold valve 8, rather than being disposed between the aseptic surge tank 19 and the head tank 11. A plurality of filtering devices arranged in parallel with each other may be provided. The filtering device may be disposed at different positions, for example, at a position upstream of the balance tank 5 or at the tip ends of the filling nozzles 2a.

As described above, the first filtering device 22a and the second filtering device 22b are arranged in parallel with each other in the filtering device. Therefore, for example, filtering of the product can be performed by the first filtering device 22a when the product is manufactured in the first manufacturing step, and can be performed by the second filtering device 22b when the product is manufactured in the second manufacturing step. In that case, while the product is being manufactured, the filtering device that is not used for filtering of the product is preferably subjected to a cleaning step of removing remaining foreign matters from the manufacturing step and an inspection operation of checking that the product does not contain rubber or metal foreign matters such as a gasket residue. By performing the cleaning operation and the inspection operation during manufacture of the product as described above, a cleaned filtering device can always be used after transition from the first manufacturing step to the second manufacturing step, and the operability of the product filling apparatus is improved.

Although the present invention is configured as described above, the present invention is not limited to the embodiment described above, and various modifications can be made within the scope of the spirit of the present invention.

REFERENCE SIGNS LIST 2 filling machine
6a upstream-side feedback path
6b downstream-side feedback path
7 drink supply piping
7a upstream-side piping section
7b downstream-side piping section
18 heating sterilization part

The invention claimed is:

1. A method of cleaning and sterilizing a drink filling apparatus that includes a drink supply piping that feeds a drink sterilized in a heating sterilization part of the drink filling apparatus to a filling machine of the drink filling apparatus, the method comprising the steps of:
  performing a cleaning in place (CIP), in which a cleaner is circulated in the drink supply piping to remove a drink residue on an interior of the drink supply piping;
  raising a temperature of the cleaner to a temperature required for a sterilizing in place (SIP) as the cleaner is circulated in the drink supply piping while performing the CIP;
  performing the SIP in succession to the CIP to sterilize the interior of the drink supply piping, wherein the CIP and the SIP are performed by circulating a cleaner in each of an upstream-side process path and a downstream-side process path, said upstream-side process path formed by an upstream-side piping section comprising a balance tank, the heating sterilization part, a manifold valve, and an upstream-side feedback path, and said downstream-side process path formed by a downstream-side piping section comprising the manifold valve, an aseptic surge tank, a head tank, the filling machine, and a downstream side feedback path, said manifold valve disconnecting the upstream-side piping section from the downstream-side piping section during said CIP and said SIP;
  coupling the upstream-side process path with the downstream-side process path with the manifold valve;
  heating and sterilizing aseptic water in the heating sterilization part;
  removing the cleaner used for the CIP and SIP by rinsing the interior of the drink supply piping with the aseptic water, wherein the aseptic water flows in the upstream-side process path and the downstream-side process path and discharging the aseptic water from the drink filling apparatus;
  after the cleaner in the upstream-side process path and the down-stream side process path is removed with the aseptic water, circulating the aseptic water in the upstream-side process path by flowing the aseptic water from the upstream-side piping section through the manifold valve and to the upstream-side feedback path;
  stopping a flow of the aseptic water to the downstream-side piping section and simultaneously or after, supplying aseptic air into the aseptic surge tank and the head tank; and
  removing the aseptic water remaining in the aseptic surge tank, the head tank, and the downstream-side piping section, thereby keeping an interior of the aseptic surge tank and the head tank at a positive pressure and maintained in an aseptic condition.

2. The method of cleaning a sterilizing a drink filling apparatus according to claim 1, wherein the aseptic water heated in the heating sterilization part has a sterilization value.

3. The method of cleaning and sterilizing a drink filling apparatus according to claim 1, further comprising a heat exchanger which heats the aseptic water, wherein the heat exchanger is arranged between the heating sterilization part and the balance tank.

4. The method of cleaning and sterilizing a drink filling apparatus according to claim 2, further comprising a heat exchanger which heats the aseptic water, wherein the heat exchanger is arranged between the heating sterilization part and the balance tank.

\* \* \* \* \*